United States Patent
Woster et al.

(10) Patent No.: US 11,834,392 B2
(45) Date of Patent: Dec. 5, 2023

(54) KDM4B INHIBITORS FOR THE TREATMENT OF INFLAMMATORY DISEASES AND DISORDERS

(71) Applicant: MUSC FOUNDATION FOR RESEARCH DEVELOPMENT, Charleston, SC (US)

(72) Inventors: Patrick M. Woster, Charleston, SC (US); Joy E. Kirkpatrick, Charleston, SC (US)

(73) Assignee: MUSC Foundation for Research Development, Charleston, NC (US)

( * ) Notice: Subject to any disclaimer, the term of this patent is extended or adjusted under 35 U.S.C. 154(b) by 240 days.

(21) Appl. No.: 16/956,871

(22) PCT Filed: Jun. 4, 2020

(86) PCT No.: PCT/US2020/036028
§ 371 (c)(1),
(2) Date: Jun. 22, 2020

(87) PCT Pub. No.: WO2020/247567
PCT Pub. Date: Dec. 10, 2020

(65) Prior Publication Data
US 2022/0119344 A1    Apr. 21, 2022

Related U.S. Application Data (60) Provisional application No. 62/856,799, filed on Jun. 4, 2019.

(51) Int. Cl.
*C07C 235/38* (2006.01)
(52) U.S. Cl.
CPC .................. *C07C 235/38* (2013.01)
(58) Field of Classification Search
CPC .................................................. C07C 235/38

USPC ......................................................... 514/485
See application file for complete search history.

(56) References Cited

U.S. PATENT DOCUMENTS 6,515,027 B1    2/2003    Bondinell et al.
2016/0158188 A1*    6/2016    Ando ..................... A61K 31/47
                                                                    514/471

OTHER PUBLICATIONS

Prasanna Datar, QSAR and Synthesis of a Novel Biphenyl Carboxamide Analogue for Analgesic Activity, 2015, Mod Chem appl, 3:1, 1-7 (Year: 2015).*
Kehl et al., Electrochemical Synthesis of 5-Aryl-phenanthridin-6-one by Dehydrogenative N,C Bond Formation, 2018, Chem. Eur. J., 24, 17230-17233 (Year: 2018).*
Rao et al., Synthesis, characterization and antimicrobial activity of novel biphenyl tetrazoles, 2012, Der Pharma Chemica, 4(3), 1093-1103 (Year: 2012).*
The International Search Report and Written Opinion, dated Nov. 9, 2020, in the corresponding PCT Patent Appl. No. PCT/US20/36028.
Henderson et al. "3D-QSAR and 3D-QSSR models of negative allosteric modulators facilitate the design of a novel selective antagonist of human 0482 neuronal nicotinic acetylcholine receptors," Bioorg Med Chem Lett, 22(4): pp. 1797-1813, Feb. 15, 2012.
Pubchem, Substance Record for SID 136925290. Available Date: Jul. 25, 2012, retrieved on Aug. 3, 2020, Retrieved from the Internet: https://pubchem.ncbi.nlm.nih.gov/substance/136925290.
The International Preliminary Report on Patentability (Chapter I), dated Dec. 16, 2021, in the corresponding PCT Appl. No. PCT/US20/36028.

* cited by examiner

*Primary Examiner* — Kristin A Vajda (57) ABSTRACT

The invention relates to KDM4B inhibitors, compositions comprising an effective amount of KDM4B inhibitors and methods for treating inflammatory diseases and disorders.

22 Claims, 5 Drawing Sheets

KDM4B INHIBITORS FOR THE TREATMENT OF INFLAMMATORY DISEASES AND DISORDERS

CROSS-REFERENCE TO RELATED APPLICATIONS

This application is a National Stage Application of PCT/US2020/036028 filed on Jun. 4, 2020, which claims priority from U.S. Provisional Patent Application No. 62/856,799 filed on Jun. 4, 2019. Each of prior mentioned applications is hereby expressly incorporated by reference herein in its entirety.

STATEMENT REGARDING FEDERALLY SPONSORED RESEARCH OR DEVELOPMENT

This invention was made with Government support under grant numbers 5R01DE029637-02, DE027290, TL1 grant TR001451 and SCTR grant TR001450. The Government has certain rights in the invention.

FIELD OF THE INVENTION

The invention relates to KDM4B inhibitors, compositions comprising an effective amount of a KDM4B inhibitor and methods for treating, for example, inflammatory diseases and disorders such as, for example, periodontal disease. In one embodiment, the KDM4B inhibitors have a biphenyl-carboxamido-benzoic acid pharmacophore.

All publications, patents, patent applications, and other references cited in this application are incorporated herein by reference in their entirety for all purposes and to the same extent as if each individual publication, patent, patent application or other reference was specifically and individually indicated to be incorporated by reference in its entirety for all purposes. Citation of a reference herein shall not be construed as an admission that such is prior art to the present invention.

BACKGROUND OF THE INVENTION

Periodontal disease, an inflammatory disease, is initiated by bacterial plaque buildup in the oral cavity which initiates a hyper-inflammatory cascade resulting in destruction of host tissues. In the absence of the biofilm following removal by the standard of care treatment of scaling and root planing, the host immune response can remain hyper-active and continued tissue damage afflicts the host. Data suggests that the periodontal disease microenvironment induces epigenetic changes, namely heightened KDM4B activity and lowered KDM1A activity, which can be reversed using pharmacological inhibitors of KDM4B.

A need exists in the art for novel KDM4B inhibitors for treating inflammatory diseases and disorders such as periodontal disease.

SUMMARY OF THE INVENTION

In one embodiment of the present invention, provided are KDM4B inhibitors having a biphenyl-carboxamido-benzoic acid pharmacophore. In other embodiments of the invention, provided are methods for treating inflammatory diseases and disorders using these KDM4B inhibitors and pharmaceutical compositions comprising said KDM4B inhibitors. In further embodiments, the disease associated with high KDM4B expression include, for example, rheumatoid arthritis, osteoarthritis, inflammatory bowel disease, multiple sclerosis, neurological disease and neurodegeneration, systemic lupus erythematosus, acute kidney disease and glomerulonephritis, asthma, seasonal and food allergies, diabetes, cardiovascular disease and reperfusion injury, and cancer.

BRIEF DESCRIPTION OF THE FIGURES

FIG. 4 shows that derivatives of 12 cause immunosuppression and were used to develop a binary QSAR model. The phenotypic immunosuppressive screen data (A) was converted into binary data using statistical significance ($P<0.05$) as a cutoff. A contingency analysis was run on the tested compounds to identify the physicochemical descriptors that were most highly correlated with activity. The top 12 descriptors from this analysis were used (Table 2) to map a quantitative structure activity relationship using Molecular Operating Environment software that had a cross-validated accuracy to predict actives of 88% and inactives of 100% (B). The combinatorial library was mapped to this model to predict which of the proposed compounds would be active (C). The data point in red represents the current lead compound, 42. The model was refined in the same manner as new activity data was made available following synthesis and in vitro analysis of 15 more compounds (A) 40 and 42 are novel, potent immunosuppressive compounds. (D) 42 (red) and 40 (blue) docked in the active site of KDM4B (gray, PDB:4LXL). The small molecules occupy the same space as the natural ligand, H3K9me3 (yellow) and the cofactor 2-oxoglutarate (yellow). $*p<0.05$, $p<0.01$, $**p<0.0001$ compared to DMSO control via one-way ANOVA with multiple comparisons.

DETAILED DESCRIPTION OF THE INVENTION

Periodontal disease (PD) afflicts 46% of Americans with no effective adjunctive therapies available. While most pharmacotherapy for PD targets bacteria, the host immune response is responsible for driving tissue damage and bone loss in severe disease. Herein, the inventors establish that the histone demethylase KDM4B is a potential drug target for the treatment of PD. Immunohistochemical staining of diseased periodontal epithelium revealed an increased abundance of KDM4B that correlates with inflammation. In murine calvarial sections exposed to *Aggregatibacter actinomycetemcomitans* lipopolysaccharide (Aa-LPS), immunohistochemical staining revealed a significant increase in KDM4B protein expression.

Figure 1:
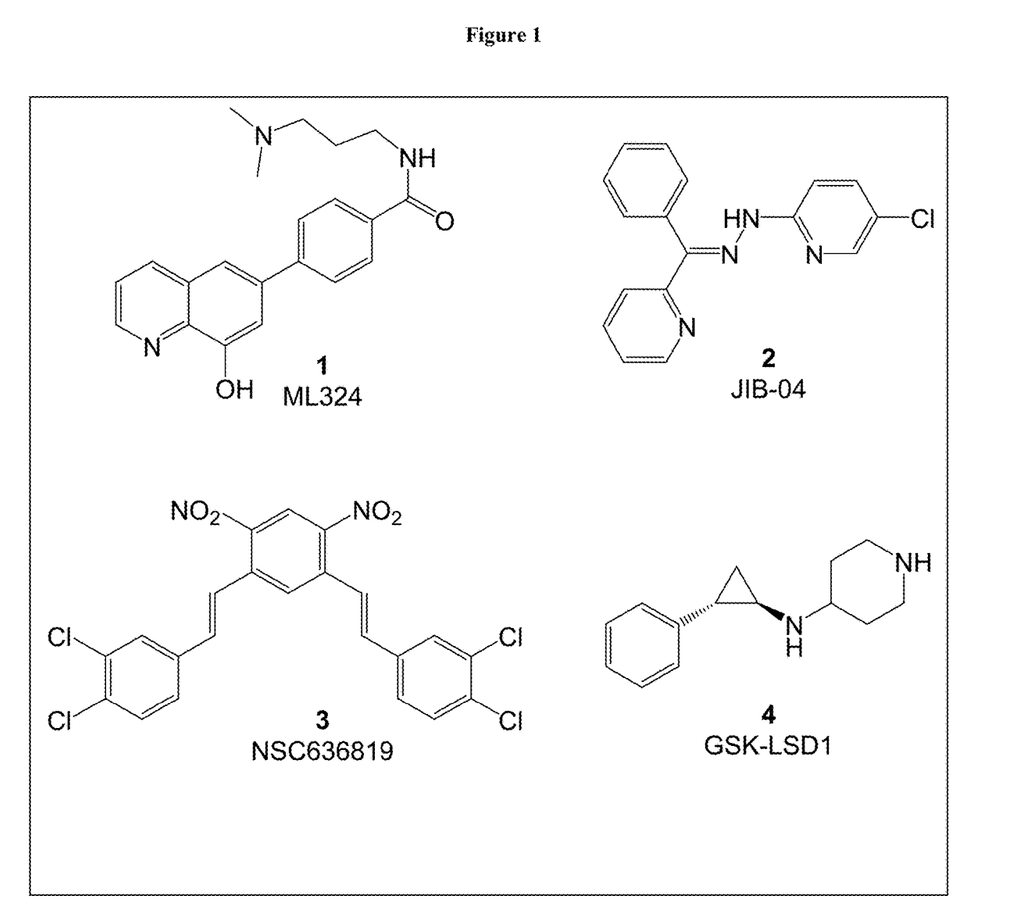
FIG. 1 shows compounds known to interact with KDM4B (compounds 1-3) and KDM1A (compound 4).

The 8-hydroxyquinoline ML324 (FIG. 1) is known to inhibit the related demethylase KDM4E in vitro, but has not been evaluated against any other targets. Studies indicate that ML324 also inhibits KDM4B, ($IC_{50}$ 4.9 µM), and decreases the pro-inflammatory cytokine response to an Aa-LPS challenge in vitro. Results suggest that KDM4B inhibition-induced immunosuppression works indirectly, requiring new protein synthesis. In addition, fluorescence-stained macrophages exhibited a significant decrease in global monomethyl histone 3 lysine 4 (H3K4me) levels following an Aa-LPS challenge that was prevented by KDM4B inhibition, suggesting this effect is produced through KDM1A-mediated demethylation of H3K4. Finally, ML324 inhibition of KDM4B in osteoclast progenitors produced a significant reduction in Aa-LPS-induced osteoclastogenesis. These data link histone methylation with host immune response to bacterial pathogens in PD, and suggest an alternative mechanism for epigenetic control of the host inflammatory environment that has not previously been reported. As such, KDM4B represents a new therapeutic target for treating hyper-inflammatory diseases that result in, for example, bone destruction.

Interestingly, macrophages play a dual role in periodontal disease depending on how polarized they are towards inflammation or resolution. Classically activated or M1 macrophages can secrete pro-inflammatory cytokines to recruit additional immune cells to the site. These macrophages are activated by exposure to lipopolysaccharide or IFN-γ. On the other hand, pro-resolving macrophages or M2 macrophages have more anti-inflammatory capabilities.[1] M2 macrophages can be further broken down into M2a, M2b, or M2c depending on their specific activating factors.[2] In periodontal disease, there is an imbalance in the M1/M2 ratio, where M1 macrophages predominate for the purpose of clearing microbes. This imbalance leads to tissue destruction characteristic of periodontal disease.[3] Many studies have been conducted to understand the dynamics that govern polarization of macrophages towards one subset or another, as tight control of these processes could prove useful therapeutically. For example, KDM4D knockdown in fibroblasts results in IL-12 gene repression.[4] IL-12 is associated with M1/Th1 immunity, as opposed to IL-10 which would drive the immune system towards M2/Th2 immunity.[5] Additionally, JMJD3 has been shown to be induced by LPS stimulation in macrophages.[6] This epigenetic enzyme demethylates H3K27me3 to H3K27me and its activity is important for macrophage polarization into the M2 or anti-inflammatory state.[7] The KDM4B/KDM1A axis is likely involved in this process heavily, as previous literature has shown that inhibition of the KDM4 family induces apoptosis in M1 macrophages and conversely introduction of a KDM1A inhibitor promotes expression of M1 markers and decreases M2 markers.[8-9]

Figure 5:
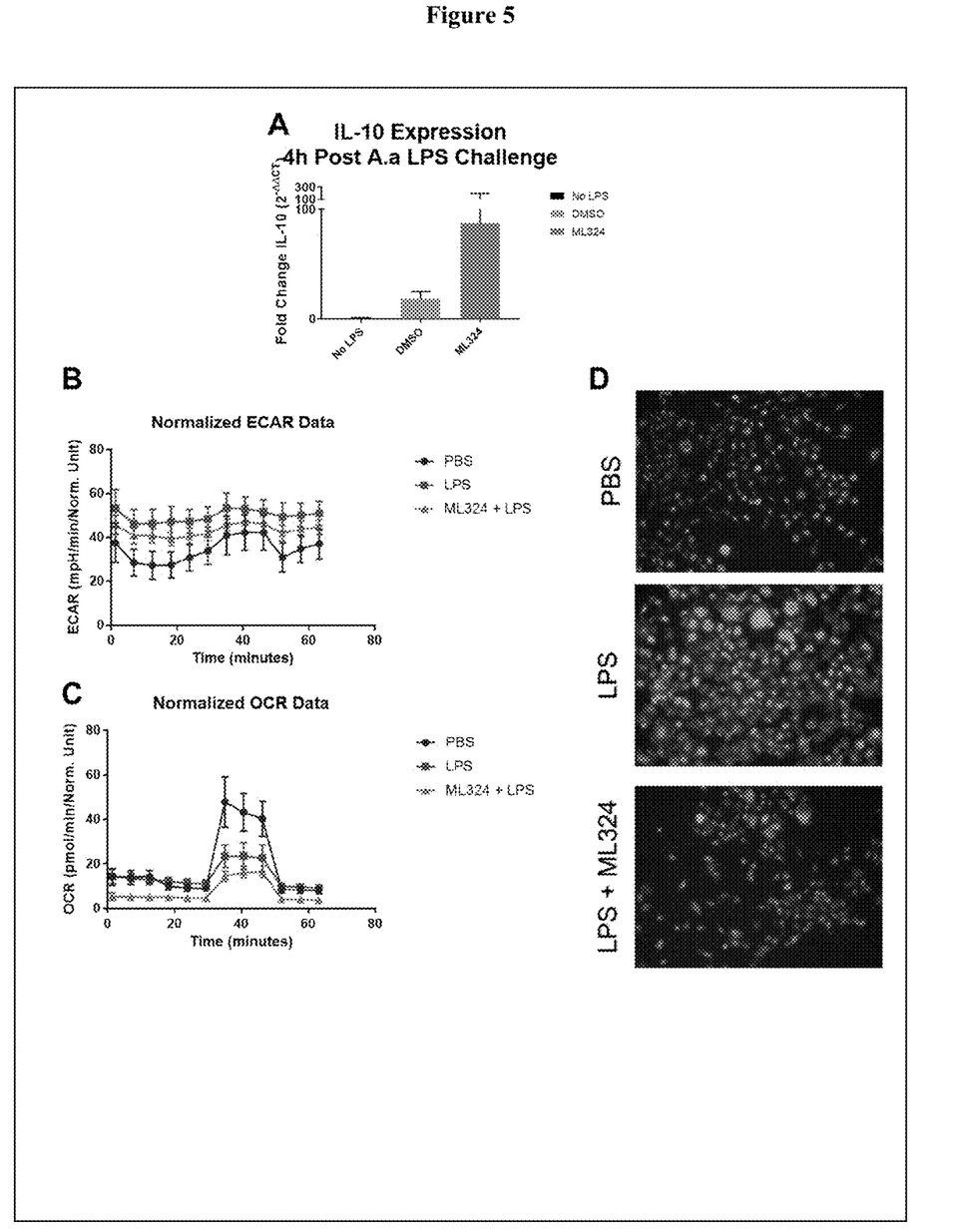
FIG. 5 illustrates that ML324 alters macrophage polarization. KDM4B inhibition alters macrophage metabolism in response to A.a LPS. Primary BMDMs were isolated and differentiated as previously described and were pre-treated with ML324 at 50 uM for 1 hour followed by A.a LPS (100 ng/mL). 24 hours later, extracellular flux was analyzed using a seahorse XFe96 instrument and following metabolic analysis, cells were incubated with phalloidin 488 and DAPI. Representative images were acquired using the Hermes Wiscan system at 10× for morphological analysis. N=4.

As previously mentioned, literature suggests that KDM4B may be involved in macrophage polarization,[8, 10-11] therefore the inventors wanted to test whether ML324-induced immunosuppression was due to M2 polarization or de-differentiation of macrophages. Primary BMDMs were isolated and differentiated as previously described and were pre-treated with ML324 at 50 µM for 1 hour followed by A.a LPS (100 ng/mL). 24 hours later, mRNA was isolated and IL-10 expression was quantified using qRT-PCR and ML324 pre-treated cells were found to have significantly higher IL-10 expression. (FIG. 5A) To determine if macrophages were M2 polarized, Extracellular flux was analyzed using a seahorse XFe96 instrument as previously described.[12] The inventors found that LPS treated cells are more glycolytic than PBS control cells, and ML324 pre-treatment rescued this effect. (FIG. 5B) Additionally, cells treated with LPS, with or without ML324 exhibit a reduced spare respiratory capacity compared to PBS control treated cells. (FIG. 5C) These data suggest that ML324 pre-treatment alters macrophage metabolism with an overall reduction in metabolic activity. To further probe macrophage polarization, the inventors fluorescently stained both the cytoplasm and nuclei of cells to visualize cell morphology, as clear morphological differences are known to exist between M0 (un- or de-differentiated macrophages), M1 (pro-inflammatory) or M2 (anti-inflammatory) macrophages.[13] The inventors found that LPS treated macrophages exhibited an M1 phenotype, and ML324 pre-treatment was able to rescue this effect, appearing very similar to PBS control treated cells. (FIG. 5D)

The exacerbated immune response of the periodontally diseased host is well known in the literature to be the source of the tissue damage and bone loss characteristic of the disease[2]. Still, therapeutic development has been aimed towards topically applied local antimicrobials such as chlorhexidine (PerioChip), doxycycline (Periostat) and minocycline (Arestin). Nevertheless, these therapies provide a moderate clinical benefit at best[3], and require heavy patient compliance with visits required as often as every three months, which is rarely covered by insurance premiums. While the microbial component of periodontal disease is indeed important to disease pathogenesis[2, 4-5], these therapies are applied by clinicians following standard of care treatment—which is to remove plaque biofilms through scaling and root planning (SRP), effectively leaving little to no microbial load immediately following treatment[5]. Disease recurrence is driven rather by a continuation of immune activation and an inability for the periodontal wounds to heal[6-7]. Given this information, one can imagine that a local immunosuppressive drug would afford some benefit, allowing the host immune system to resolve, wounds to heal, and ultimately preventing disease recurrence. The failure of previously explored anti-inflammatory agents is likely due to their surface level targets such as secreted effector proteins that do not cause heritable changes beyond single cell divisions. Epigenetic therapeutics offer an advantage in this regard as they seek to reverse detrimental environmental changes that have the ability to propagate harmful disease processes.

In 2012, the NIH molecular libraries program reported the discovery of N-(3-(dimethyamino)propyl-4-(8-hydroxyquinolin-6-yl)benzamide(1), a small molecule inhibitor specifically targeting KDM4E[8]. While this compound was shown to inhibit viral replication of herpes simplex virus and cytomegalovirus in mice at high doses[9], the compound was not probed for additional activity. The inventors recently reported that 1 is active toward a closely related enzyme, KDM4B, and has immunosuppressive action in murine macrophages[1]. While this compound exhibits good cell permeability, it is highly insoluble at effective doses and requires a 14-step synthesis for development of new derivatives[8]. Because of this, the inventors sought to determine novel scaffolds with the potential to inhibit KDM4B, cause immunosuppressive effects, and potentially serve as developmental compounds for localized treatment of periodontal disease.

The inventors herein utilized a multidisciplinary approach that combined consensus computational docking data with phenotypic screens using primary murine macrophages to identify a derivatizable scaffold with KDM4B inhibitory action. The inventors further used this strategy to generate the lead compounds and ultimately identified compound 25 as an example of a potent compound that could be used to treat periodontal disease.

Definitions

The following definitions are used in connection with the KDM4B inhibitors:

The term "KDM4B inhibitors" includes any and all possible isomers, stereoisomers, enantiomers, diastereomers, tautomers, pharmaceutically acceptable salts, hydrates, solvates, and prodrugs of the KDM4B inhibitors described herein.

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

Unless otherwise specifically defined, the term "aryl" refers to cyclic, aromatic hydrocarbon groups that have 1 to 2 aromatic rings, including monocyclic or bicyclic groups such as phenyl, biphenyl or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. The substituents can themselves be optionally substituted.

The term "alkyl" as used herein denotes an unbranched or branched chain, saturated, monovalent hydrocarbon residue containing 1 to 20 carbon atoms. In one embodiment, the number of carbon atoms in the alkyl chain can be 2, 3, 4, 5, 6, 7, 8, 9, 10, 11, 12, 13, 14, 15, 16, 17, 18, 19 or 20 carbon atoms. In another embodiment, the number of carbon atoms in the alkyl chain can be from 5 to 16 and referred to as "$(C_5-C_{16})$alkyl."

The term "lower alkyl" denotes a straight or branched chain hydrocarbon residue containing 1 to 6 carbon atoms. "$C_{1-20}$ alkyl" as used herein refers to an alkyl composed of 1 to 20 carbons. Examples of alkyl groups include, but are not limited to, lower alkyl groups include methyl, ethyl, propyl, i-propyl, n-butyl, i-butyl, t-butyl, pentyl, isopentyl, neopentyl, hexyl, heptyl, octyl, nonyl, decyl, undecyl, dodecyl, tridecycl and hexadecyl.

The term "alkoxy" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined. "$C_{1-10}$ alkoxy" as used herein refers to an-O-alkyl wherein alkyl is $C_{1-10}$.

The terms "aryl" or "heteroaryl" as used herein include but are not limited to, indolyl, isoindolyl, isoindolinyl, indazolyl, benzofuranyl, benzothienyl, benzothiazolyl, benzothiazolonyl, benzoxazolyl, benzoxazolonyl, benzisoxazolyl, benzisothiazolyl, benzimidazolyl, benzimidazolonyl, benztriazolyl, imidazopyridinyl, dihydropurinonyl, pyrrolopyrimidinyl, purinyl, pyrazolopyridinyl, pyrazolopyrimidinyl, phthalimidyl, phthalimidinyl, pyrazinylpyridinyl, pyridinopyrimidinyl, pyrimidinopyrimidinyl, cinnolinyl, quinoxalinyl, quinazolinyl, quinolinyl, isoquinolinyl, quinolonyl, isoquinolonyl, phthalazinyl, benzodioxyl, indolinyl, benzi sobiazoline-1,1,3-trionyl, dihydroquinolinyl, tetrahydroquinolinyl, dihydroisoquinolyl, tetrahydroisoquinolinyl, benzoazepinyl, benzodiazepinyl, benzoxapinyl, benzoxazepinyl, phenyl, naphthyl, pyrrolyl, furyl, thienyl, oxazolyl, thiazolyl, isoxazolyl, isothiazolyl, imidazolyl, pyrazolyl, oxadiazolyl, thiadiazolyl, triazolyl, tetrazolyl, pyridinyl, pyrimidinyl, pyrazinyl, pyridazinyl, and triazinyl.

The term "cycloalkyl" refers to a cyclic hydrocarbon containing 3-6 carbon atoms. Examples of a cycloalkyl group include, but are not limited to, cyclopropyl, cyclobutyl, cyclopentyl and cyclohexyl. It is understood that any of the substitutable hydrogens on a cycloalkyl can be further substituted.

The term "halogen" as used herein means fluorine, chlorine, bromine or iodine. In one embodiment, halogen may be fluorine or bromine.

The term "heterocycle" as used herein refers to a cyclic hydrocarbon containing 3-6 atoms wherein at least one of the atoms is an O, N, or S wherein a monocyclic heterocycle may contain up to two double bonds. Examples of heterocycles include, but are not limited to, aziridine, oxirane, thiirane, azetidine, oxetane, thietane, pyrrolidine, tetrahydrofuran, tetrahydrothiophene, piperidine, tetrahydropyran, thiane, imidazolidine, oxazolidine, thiazolidine, dioxolane, dithiolane, piperazine, oxazine, dithiane, and dioxane.

A "subject" is a mammal, e.g., a human, mouse, rat, guinea pig, dog, cat, horse, cow, pig, or non-human primate, such as a monkey, chimpanzee, baboon or rhesus, and the terms "subject" and "patient" are used interchangeably herein.

The invention also includes pharmaceutical compositions comprising an effective amount of an KDM4B inhibitor and a pharmaceutically acceptable carrier. The invention includes an KDM4B inhibitor provided as a pharmaceutically acceptable prodrug, hydrate, salt, such as a pharmaceutically acceptable salt, enantiomers, stereoisomers, or mixtures thereof.

Representative "pharmaceutically acceptable salts" include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bi s-2-hydroxy-3- naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

The term "carrier," as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body.

The term "treating," with regard to a subject, refers to improving at least one symptom of the subject's disorder. Treating can be curing, improving, or at least partially ameliorating the disorder.

The term "disorder" is used in this disclosure to mean, and is used interchangeably with, the terms disease, condition, or illness, unless otherwise indicated.

The term "administer," "administering," or "administration" as used in this disclosure refers to either directly administering a compound or pharmaceutically acceptable salt of the compound or a composition to a subject, or administering a prodrug derivative or analog of the compound or pharmaceutically acceptable salt of the compound or composition to the subject, which can form an equivalent amount of active compound within the subject's body.

The term "prodrug," as used in this disclosure, means a compound which is convertible in vivo by metabolic means (e.g., by hydrolysis) to an KDM4B inhibitor.

The term "optionally substituted," as used in this disclosure, means a suitable substituent can replace a hydrogen bound to a carbon, nitrogen, or oxygen. When a substituent is oxo (i.e., =O) then 2 hydrogens on the atom are replaced by a single O. Suitable substituents are selected from the following which include, but are not limited to, hydroxyl, halogen, perfluorinated $C_1$-$C_6$ alkyl, amine, —$C_1$-$C_{12}$ alkyl, —$C_2$-$C_{12}$ alkene, —$C_2$-$C_{12}$ alkyne, —($C_1$-$C_3$ alkyl)-(cycloalkyl), aryl, alkyl-aryl, —C(O)H, —C(O)OH, —C(O)alkyl, —C(O)—O-alkyl, —C(O)NH(alkyl), benzyl, —C(O)NH$_2$, —C(O)N(alkyl)$_2$, —NHC(O)H, —NHC(O)alkyl, —SO$_2$(alkyl), —SO$_2$NH$_2$, —SO$_2$NH(alkyl), —SO$_2$N(alkyl)$_2$, S, CN, and SCN. It will be understood by those skilled in the art, with respect to any group containing one or more substituents, that such groups are not intended to introduce any substitution or substitution patterns that are sterically impractical, synthetically non-feasible and/or inherently unstable. Furthermore, combinations of substituents and/or variables within any of the Formulae represented herein are permissible only if such combinations result in stable compounds or useful synthetic intermediates wherein stable implies a reasonable pharmologically relevant half-life at physiological conditions.

Identification and Synthesis of Representative Compounds of the Invention

Figure 2:
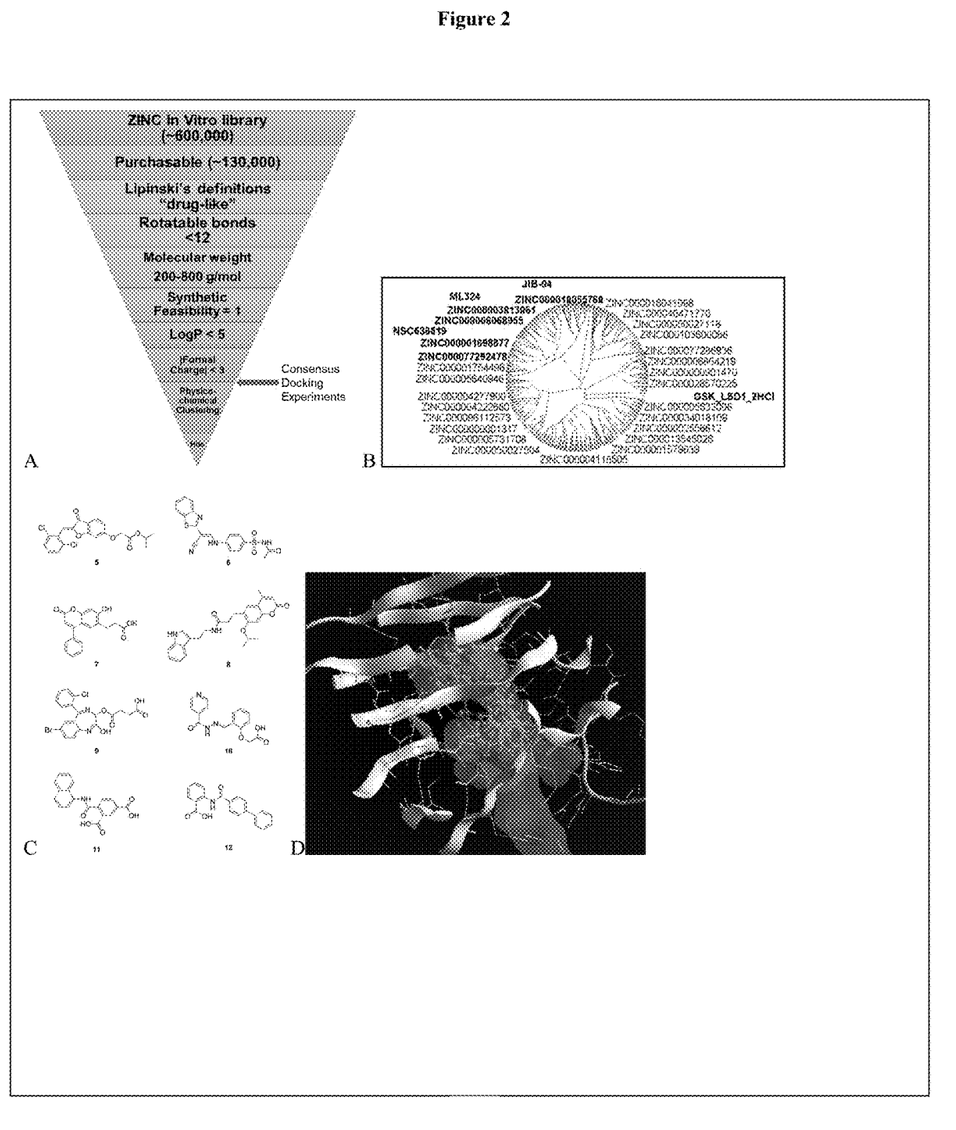
FIG. 2 illustrates an orthogonal in silico docking strategy that yielded novel and commercially available immunosuppressive compounds. The public ZINC compound database was filtered and refined prior to docking to increase computational efficiency as well as after docking to eliminate PAINS and false positives/negatives (A). Compounds that ranked in the top 70% of both docks were physicochemically clustered and the cluster containing ML324 and JIB-04 was sorted based on binding affinity (B). The top 8 compounds (C) were purchased from Vitas laboratories. Compounds overlay space taken by natural ligands (D) 2-oxoglutarate (green), H3K9me3 (teal), KDM4B (pink, PDB: 4LXL), top 8 hits (orange), ML324 (red).

The ZINC database of molecules[10] was filtered to retrieve compounds that were proposed to have in vitro activity as well as compounds that could be purchased. This library was further filtered to remove any potential pan-assay interference compounds (PAINS)[11] as well as compounds with Lipinski violations, cytotoxic or unfavorable features[12] (FIG. 2A). The remaining compounds were subjected to high throughput screening for activity towards the KDM4B active site using two separate software programs (DOCK6.5, Molecular Operating Environment). The consensus activity data[13] was consolidated into 8,000 top compounds that were clustered based on physicochemical properties[14] (FIG. 2B) and the top compounds that were physicochemically similar to previously identified KDM4B inhibitors[8, 15-16] were purchased for in vitro evaluation (FIG. 2C, D).

Several compounds from this initial clustered data set were active and suppressed the immune response to A.a LPS at 50 μM (FIG. 2A). The inventors decided to move forward with 11 because of the three membered structure and multiple routes of straight forward combinatorial chemistry-based synthesis. Before Investing significant time in development of derivatives of 12, the inventors confirmed a dose-dependent immunosuppressive response to A.a LPS (FIG. 2B) with a concurrent increase in H3K9me3 (FIG. 2C), suggesting the effect was on-target.

Sixteen derivatives (Example 1, Table 1; 13-28 below) were synthesized using a 5-step microwave assisted synthesis from derivatized bromobenzenes, phenyltrifluorborates and 2-amino benzoates (Scheme 1). Potential compounds were developed in silico, using commercially available and economical starting materials. This library was docked to the active site of KDM4B using consensus screening and hits were ranked based on binding affinity. Top derivatives predicted by consensus scores as well as easy to synthesize derivatives were synthesized. The first step of synthesis was a microwave assisted Suzuki coupling of a bromobenzene and trifluoroborate to yield a two-ringed ester. The second step was microwave-assisted saponification to cleave the ester into a reactive carboxylic acid. The third step was further activated the carbonyl into a carbonyl chloride followed by addition of an aminobenzoate under basic conditions to yield the final three-membered ester. The resulting ester was cleaved in the final step using the same microwave-assisted saponification reaction to increase solubility of the final compounds.

Derivatives were monitored for in vitro immunosuppressive activity using the previously described periodontal disease inflammation model[1] using primary murine macrophages. 22, 24, 32 caused a significantly reduced secretion of the pro-inflammatory cytokine, IL-6, in response to A.a LPS. (FIG. 3A) resulting in an overall hit rate of 20%. Compounds that significantly reduced inflammatory cytokine production compared to DMSO controls as determined by one-way ANOVA with multiple comparisons were set as actives while those that did not were set as inactives. These data were consolidated into a binary quantitative structure activity relationship, where descriptors were chosen based on contingency analysis as shown in Table 2:

TABLE 2

Descriptors Used for Development of Binary Quantitative Structure Activity Relationship.

| Physicochemical Descriptor | Descriptor Class |
|---|---|
| balabanJ | Adjacency and distance matrix |
| BCUT_SLOGP_2 | |
| diameter | |
| GCUT_PEOE_1 | |
| radius | |
| VDistEq | |
| wienerPath | |
| wienerPol | |
| Kier2 | Kier and Hall connectivity and kappa shape |
| Kier3 | |
| KierA3 | |
| PEOE_VSA+0 | Partial charge |

Model 1 was using the original training set with 18 compounds (12, 19-33).

Figure 4:
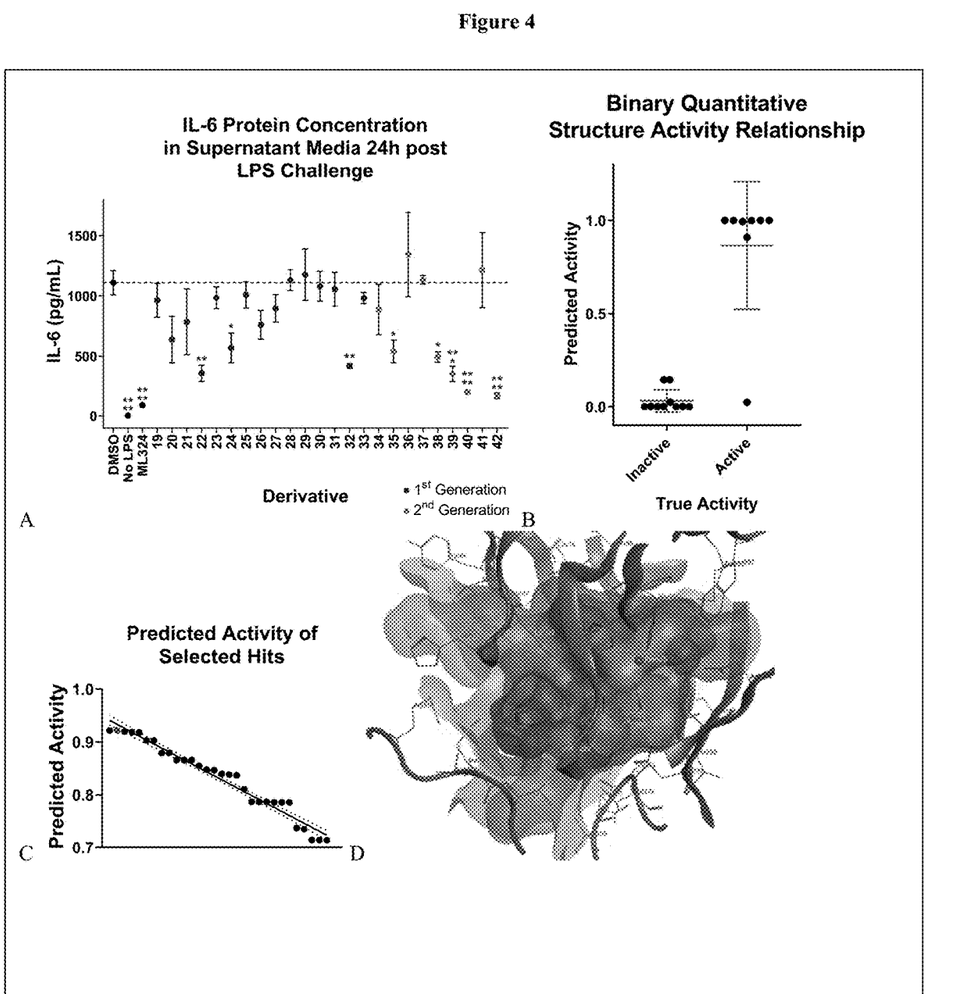

This model had a 88% accuracy to predict active hits and a 100% accuracy to predict inactive compounds (FIG. 4B). The model was applied to the in silico library of derivatives and yielded multiple potential hits with greater than 70% chance of being active. More importantly, several hits were eliminated from the pool of potential hits with high confidence.

The second generation of inhibitors was synthesized (Example 1, Table 1, below) and compound 35, 38-40 and 42 significantly reduced the secretion of IL-6 in response to A.a LPS in vitro. (FIG. 4A) The QSAR was updated with the second generation activity data for future studies (Table 2), but the current lead compounds were further evaluated because of their potent immunosuppressive action rivaling that of the control compound, 1. The inventors found that Compounds 40 and 42 not only exhibited potent immunosuppressive action in response to periopathogenic LPS, but did this in a KDM4B-dependent manner. IC50s were determined.

The inventors utilized an in silico docking approach to identify several hit compounds for deveopment. The strategy utilized the consensus hits between multiple docking algorithms within two different software programs (DOCK6.5 flexible dock and Molecular Operating Environment rigid receptor dock) to eliminate potential false negatives. Prior to docking, the inventors selected the ZINC library containing compounds with predicted in vitro activity that were also available for sale. The inventors filtered this compound library by eliminating compounds that were not drug-like following Lipinski's rules, had many rotatable bonds and thus, had predicted cytotoxicity, and compounds that were not easy to synthesize in a high throughput manner (FIG. 2A). This refined library was docked into the active site of KDM4B and hits that ranked highly (>70th percentile) within both programs (FIG. 2C,D) were subjected to physicochemical clustering.' The inventors generated a set of OpenBabel descriptors for each compound and clustered them based on similarity to each other as well as similarity to known KDM4B inhibitors (ML324[8] 1, JIB-04[15] 2 and NSC636819[16] 3). The inventors selected the smallest grouping that contained all three of these inhibitors and made sure that this grouping did not contain the control compound, a KDM1A inhibitor. (FIG. 2B)

Figure 3:
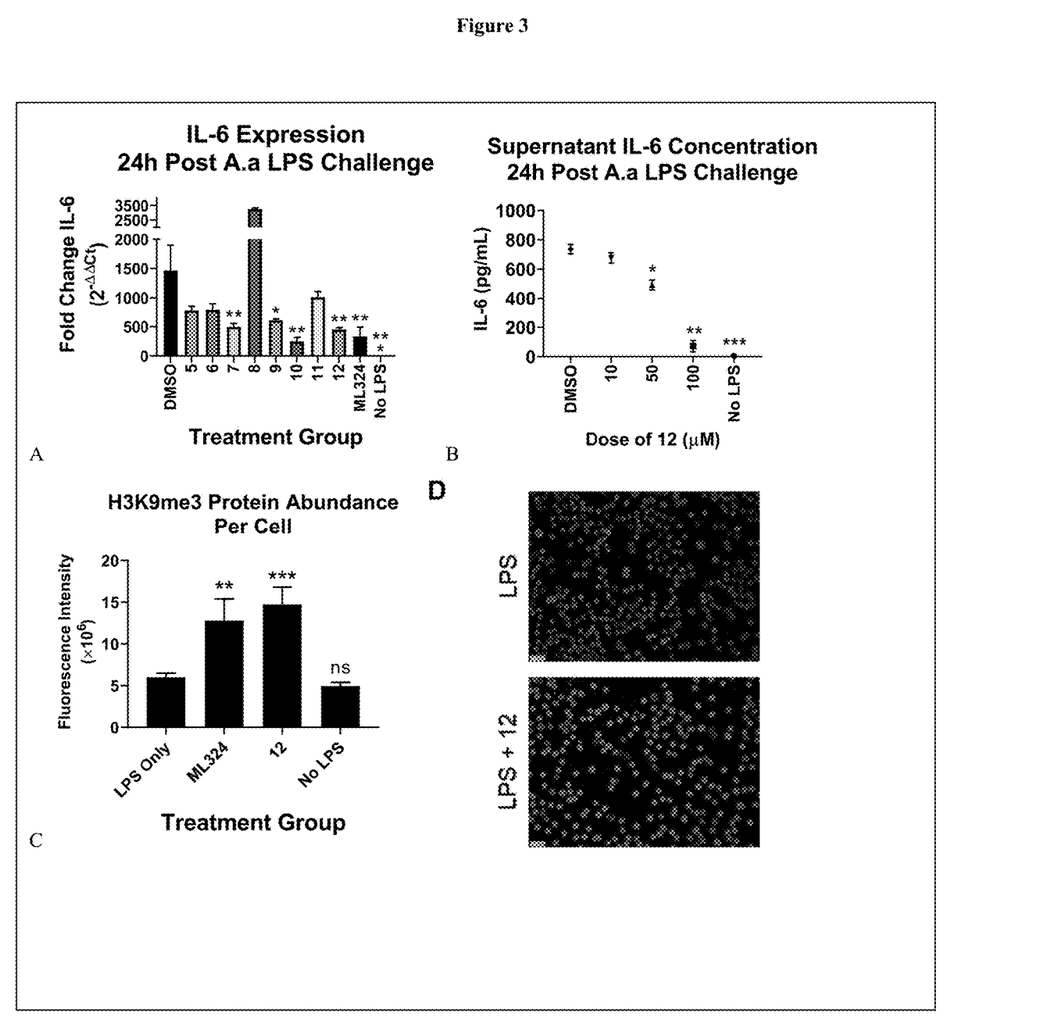
FIG. 3 shows screening data for compounds identified by in silico docking. Several initial hits suppressed the immune response to A.a LPS in vitro. (A) n=2 Compound 12 was further evaluated for dose-dependent immunosuppression. (B) as well as for increased H3K9me3 expression to confirm KDM4B inhibitory activity. (C, D) n=4. $*p<0.05$, $p<0.01$, $*p<0.001$ compared to DMSO control via one-way ANOVA with multiple comparisons.

The inventors screened the purchased hits using a previously published[1] periodontal disease immunosuppression model using primary murine macrophages challenged with *Aggregatebacter actinomycetemcomitans* lipopolysaccharide for 24 hours following 1 hour pre-treatment at 50 μM with each compound. (FIG. 3A) It is of importance in these experiments to use primary cells from normal mice as KDM4B has been established as a therapeutic target for anti-cancer agents.[16, 18] The inventors' experiments yielded several potential hits from the initial screen of several different chemotypes including anti-anxiolytic cinazepam[19] 9 and anti-tuberculosis drug aconiazide[20] 10. The inventors ultimately selected 2-([1,1'-biphenyl]-4-carboxamido)benzoic acid 12 due to its potency, solubility, ease of derivatization as well as ease of overall synthesis. The inventors first confirmed a dose-dependent immunosuppressive effect (FIG. 3B) concurrent with an increase in H3K9me3 staining (FIG. 3C,D), consistent with KDM4B inhibition. The inventors divided the scaffold into three units, each containing a benzene ring available for derivatization. The inventors generated a combinatorial library in silico based on commercially available and economical starting materials. The inventors' initial library was subjected to consensus docking to prioritize the synthetic efforts. Despite the awareness of the power in using this tool, the inventors ultimately synthesized both compounds with high binding affinity as well as compounds that the inventors were able to synthesize efficiently. For example, the parent scaffold (scaffold 1) had a simplified synthetic scheme because of the purchasability of a two ringed starting material, eliminating the bulk of the synthetic difficulty.

The Suzuki coupling reaction resulted in homocoupling of the bromobenzene starting material, which had been previously reported.[21] Additionally, the third step sometimes generated an anyhydride product for selected diphenyl carboxylic acids. The inventors hypothesize that the nucleophilic amine starting material was stabilized by the carboxylic acid hydroxy group. Because of this, several hits were synthesized based on the ability to purchase starting materials that eliminated steps in the method (biphenyl carboxylic acids 15, eliminating the Suzuki coupling and ester cleavage reactions) as well as compounds that were very reactive or could be used in heavy excess due to the high yield of the previous step.

Synthetic method (Scheme 1, below) was relatively simple and utilized microwave assisted reactions to reduce the total time for synthesis:

Scheme 1.
Synthetic method for development of benzamidobenzoic acid KDM4B inhibitors R = H, Me, OMe
X = H, F, Cl Purification of the three-ringed product 18 from the amine starting material 17 proved unexpectedly difficult, likely due to strong hydrogen bonding between the amine hydrogen and the lone pairs of the adjacent acetate oxygen. For this reason, reactions were crystallized rather than purified by column chromatography whenever possible. In the second step, the inventors found that lyophilization of the starting material 15 as well as removing the excess oxalyl chloride prior to adding the nucleophilic amine 17 were important for the success of this step. To do this more efficiently, the inventors used dry DCE rather than DCM as was previously published,[22] due to its higher boiling point. At this point, all reactions were bright yellow in color. For the next step the inventors pre-stirred triethylamine with the amine 17, and this solution was added via cannula transfer to the reaction under nitrogen. When using lower equivalents of triethylamine the reaction did not proceed, likely due to strong hydrogen bonding between the amine hydrogen and the lone pairs of the adjacent acetate oxygen which decreased the nucleophilicity of the amine. When successful, the reaction proceeded almost instantaneously, with a sharp color change and white gas occurring in almost every reaction. Unfortunately, the final step was important to the solubility of the final compounds. Thus, the ester 18 of each drug could not be considered for in vitro testing due to poor solubility. Purity of the final compounds was confirmed using UPLC, and compounds were characterized by NMR. Final compounds were only utilized for biological evaluation if purity was >95% by UPLC.

The inventors utilized the immunosuppressive action (FIG. 4A) of the first 15 (12-19-33) compounds synthesized to build a quantitative structure activity relationship (FIG. 4B) utilizing 11 descriptors. The inventors chose to use contingency analysis for selection of descriptors so that the methodology would be reproducible. The inventors had a 20% hit rate with a 100% probability to predict negative hits but only a 88% probability to predict positive hits. This model was used to guide synthesis of 9 more compounds (34-42), several of which showed a significantly higher efficacy than the first series of inhibitors (FIG. 4A), with a hit rate within the second generation of 56% yielding an overall hit rate of 29%. Interestingly, neither 40 nor 42 seem to act as substrate analogues. Rather, the amidobenzoate group may act as a 2-oxoglutarate mimic.

Thus, the inventors were able to use high-throughput computational chemical consensus screens coupled with in vitro phenotypic screening to identify a novel KDM4B inhibitor series. The inventors developed these with the phenotypic screening data to identify multiple potent KDM4B inhibitors. This study lends credence to utilizing a phenotypic approach to drug discovery and can prove particularly useful when an enzyme assay is not available or is extremely costly. The inventors conclude that novel KDM4B inhibitor scaffolds have been identified that could serve useful in treating periodontal disease through a unique epigenetic mechanism.

Methods for Using KDM4B Inhibitors

In another aspect, methods of treating or preventing a disease or disorder associated with KDM4B expression is provided, which comprises administering to a subject in need thereof, a therapeutically-effective amount of an KDM4B inhibitor. In one embodiment, the disease associated with high KDM4B expression is an inflammatory disease or disorder. In other embodiments, the diseases and disorders include, for example, rheumatoid arthritis, osteoarthritis, inflammatory bowel disease, multiple sclerosis, neurological disease and neurodegeneration, systemic lupus erythematosus, acute kidney disease and glomerulonephritis, asthma, seasonal and food allergies, diabetes, cardiovascular disease and reperfusion injury, and cancer.

The invention also includes pharmaceutical compositions useful for treating or preventing an KDM4B associated disease or disorder, or for inhibiting an KDM4B associated disease, or more than one of these activities. The compositions can be suitable for internal use and comprise an effective amount of an KDM4B inhibitor and a pharmaceutically acceptable carrier.

The KDM4B inhibitors can be administered in amounts that are sufficient to treat an inflammatory disease or disorder such as, for example, periodontal disease. Administration of the KDM4B inhibitors can be accomplished via any mode of administration for therapeutic agents. These modes include systemic or local administration such as oral, nasal, parenteral (intravenous), intramuscular, intrathecal, intravitreal, transdermal, subcutaneous, vaginal, buccal, rectal, topical administration modes or as a drug-eluting stent.

Depending on the intended mode of administration, the compositions can be in solid, semi-solid or liquid dosage form, such as, by way of non-limiting examples, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (non-limiting examples include bolus and infusion), intraperitoneal, intrathecal, intra-vitreal injection, subcutaneous or intramuscular form, all using forms well known to those skilled in the pharmaceutical arts.

Non-limiting illustrative pharmaceutical compositions are tablets and gelatin capsules comprising an KDM4B inhibitor and a pharmaceutically acceptable carrier, such as: a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, alginic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

Liquid, particularly injectable, compositions can, for example, be prepared by dissolution, dispersion, etc. For example, the KDM4B inhibitor is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the KDM4B inhibitors.

The KDM4B inhibitors can be also formulated as a suppository that can be prepared from fatty emulsions or suspensions; using polyalkylene glycols such as propylene glycol, as the carrier.

In further embodiments, the pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, delayed release formulations, extended release formulations, pulsatile release formulations, multiparticulate formulations, and mixed immediate and controlled release formulations The KDM4B inhibitors can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564, the contents of which are herein incorporated by reference in their entirety.

KDM4B inhibitors can also be delivered by the use of monoclonal antibodies as individual carriers to which the KDM4B inhibitors are coupled. The KDM4B inhibitors can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxidepolylysine substituted with palmitoyl residues. Furthermore, the KDM4B inhibitors can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels. In one embodiment, KDM4B inhibitors are not covalently bound to a polymer, e.g., a polycarboxylic acid polymer, or a polyacrylate.

Parenteral injectable administration is generally used for subcutaneous, intramuscular or intravenous injections and infusions. Injectables can be prepared in conventional forms, either as liquid solutions or suspensions or solid forms suitable for dissolving in liquid prior to injection.

Compositions can be prepared according to conventional mixing, granulating or coating methods, respectively, and the present pharmaceutical compositions can contain from about 0.1% to about 80%, from about 5% to about 60%, or from about 1% to about 20% of the KDM4B inhibitor by weight or volume.

A "therapeutically effective amount" when used in connection with an KDM4B inhibitor is an amount effective for treating or preventing an KDM4B-associated disease or disorder. The dosage regimen utilizing the KDM4B inhibitor is selected in accordance with a variety of factors including type, species, age, weight, sex, race, diet, concomitant medications, and medical condition of the patient; the severity of the condition to be treated; the route of administration; the renal or hepatic function of the patient; and the particular KDM4B inhibitor employed. A physician or veterinarian of ordinary skill in the art can readily determine and prescribe the effective amount of the drug required to prevent, counter or arrest the progress of the condition.

Therapeutically effective amounts of the present invention, when used for the indicated effects, range from about 0.1 mg to about 5000 mg of the active ingredient per unit dose which could be administered. In one embodiment, the compositions are in the form of a tablet that can be scored. Appropriate dosages of the KDM4B inhibitors can be determined as set forth in Goodman, L. S.; Gilman, A. The Pharmacological Basis of Therapeutics, 5th ed.; MacMillan: New York, 1975, pp. 201-226, the contents of which are hereby incorporated by reference.

KDM4B inhibitors can also be administered in a single daily dose, or the total daily dosage can be administered in divided doses of two, three or four times daily. Furthermore, KDM4B inhibitors can be administered in intranasal form via topical use of suitable intranasal vehicles, or via transdermal routes, using those forms of transdermal skin patches well known to those of ordinary skill in that art. To be administered in the form of a transdermal delivery system, the dosage administration can be continuous rather than intermittent throughout the dosage regimen. Other illustrative topical preparations include creams, ointments, lotions, aerosol sprays and gels, wherein the concentration of the KDM4B inhibitor ranges from about 0.1% to about 15%, w/w or w/v.

EXAMPLES

The disclosure is further illustrated by the following examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

The methodologies described herein and below are designed to (1) quantitate and describe the nature of the physical interaction between KDM4B and candidate compounds, (2) determine the biological consequence resulting from the interaction of KDM4B with the candidate compound, (3) evaluate the impact of the candidate compound in animal models of KDM4B mediated disease.

It is to be understood that any embodiments listed in the Examples section are embodiments of the KDM4B inhibitors and, as such, are suitable for use in the methods and compositions described above.

All solvents and chemicals were reagent grade. Anhydrous dichloromethane (DCM) and dichloroethane (DCE) were purchased from VWR. All solutions were dried over anhydrous magnesium sulfate or sodium sulfate, solvents were removed by rotary evaporation under reduced pressure. Solids used in dry reactions were additionally freeze dried before use. Microwave reactions were run in a Biotage Initiator. Flash column chromatography was carried out using pre-packed silica columns from RediSep or SiliCycle and mixtures adsorbed onto isolute for elution. Purity of compounds was >95% as determined by ultra-pure liquid chromatography analysis. NMR spectra were recorded on a Bruker 400 MHz instrument using $CDCl_3$, MeOD or $DMSOd_6$ as solvents. Chemical shifts are reported in ppm relative to TMS (0.00 ppm) or solvent peaks as an internal reference. Splitting patterns are indicated as follows: s, singlet; d, doublet; t, triplet; q, quartet; m, multiplet.

All data are represented as geometric mean±standard error of the mean (SEM) and statistical significance was determined using One-Way ANOVA with multiple comparisons ($p<0.05$).

Example 1

Representative Compounds of the Invention

Using the procedures that follow and those disclosed above, the following compounds were made:

TABLE 1

Novel KDM4B Inhibitors Synthesized.

| Compound | Scaffold | $R_1$ | $R_2$ | $R_3$ | $R_4$ | $R_5$ | $R_6$ | $R_7$ |
|---|---|---|---|---|---|---|---|---|
| 12 | 1 | H | COOH | H | H | H | H | H |
| 19 | 1 | H | COOH | H | H | H | CH3 | H |
| 20 | 1 | H | COOH | H | F | H | H | H |
| 21 | 1 | H | COOH | H | H | H | F | H |
| 22 | 1 | H | COOH | H | H | F | H | H |
| 23 | 1 | H | H | COOH | H | H | H | H |
| 24 | 1 | H | H | H | COOH | H | H | H |
| 25 | 2 | H | COOH | H | F | H | H | H |
| 26 | 2 | H | COOH | H | H | F | H | H |
| 27 | 3 | H | H | COOH | H | H | H | H |
| 28 | 3 | H | H | COOH | H | H | H | CH3 |
| 29 | 3 | H | H | COOH | H | F | H | H |
| 30 | 3 | H | H | COOH | H | H | H | H |
| 31 | 3 | H | H | H | COOH | H | H | H |
| 32 | 3 | CH3 | H | COOH | H | H | H | CH3 |
| 33 | 3 | O—Me | H | COOH | H | H | H | H |
| 34 | 2 | H | COOH | H | H | F | CH3 | H |
| 35 | 2 | H | COOH | H | H | F | H | H |
| 36 | 3 | H | H | COOH | H | H | H | CH3 |
| 37 | 3 | H | H | COOH | H | H | H | H |
| 38 | 1 | CH3 | COOH | H | F | H | H | H |
| 39 | 3 | CH3 | H | COOH | H | F | H | H |

TABLE 1-continued

Novel KDM4B Inhibitors Synthesized.

| Compound | Scaffold | $R_1$ | $R_2$ | $R_3$ | $R_4$ | $R_5$ | $R_6$ | $R_7$ |
|---|---|---|---|---|---|---|---|---|
| 40 | 3 | H | O—Me | COOH | H | H | H | CH3 |
| 41 | 2 | CH3 | COOH | H | H | H | CH3 | H |
| 42 | 2 | H | COOH | H | H | H | H | H |

Scaffold 1

Scaffold 2

Scaffold 3

Computational Chemistry

DOCK6.5: The KDM4B crystal structure (PDB: 4LXL) was prepared using UCSF Chimera following DOCK6.5 protocols.[23] Ligands and water molecules were removed from the crystal structure. The ZINC compound database was filtered for predicted in vitro activity in combination with compounds that were purchasable using its online sorting tools[24] This library was further refined by generating descriptors in Molecular operating environment software in a high-throughput manner and eliminating large numbers of compounds based on these unfavorable descriptors: violation of one or more of Lipinski's rules, molecular weight less than 250 and greater than 500 g/mol, greater than 12 rotatable bonds, compounds with a formal charge<−2 or >2 and the library was charged and energy pre-minimized for each structure based on standard protocols. The compound library was docked using DOCK6.5 in an unbiased manner by using the entire enzyme as the active site for docking in flexible mode with 1000 maximum orientations per computation. The compound library was concurrently docked using Molecular Operating Environment in a rigid receptor dock constrained to the active site identified by the site finder tool in MOE. Hits from both programs were ranked based on the percentage of the maximum binding energy of each hit. Compounds that ranked independently within the top 70% of both docking experiments were selected for physicochemical clustering. OpenBabel descriptors were generated for the top 70% consensus hits using Chemmine cheminformatics online tools.[1] Compounds were clustered by similarity and hits clustered in the smallest Glade containing ML324, JIB-04 and NSC636819 were selected for in vitro evaluation. This consensus docking strategy was performed on a combinatorial library of novel compounds as needed to prioritize synthetic efforts.

Primary Bone Marrow Culture

Primary bone marrow was cultured into macrophages as described previously[25]. Briefly, bone marrow from left and right femurs and tibiae of 12-14-week old wild type C57BL/6 mice was flushed into α-MEM (Corning, Cat#10-022-CV) supplemented with 10% fetal bovine serum (Hyclone, Cat #SH30071.03HI) and 1% penicillin streptomycin (Sigma, Cat #P4333) and plated overnight at 37° C. in 5% $CO_2$. Cells remaining in suspension were differentiated into experimental wells at a concentration of 2E6 cells/mL for 7 days or until 80% confluency and homogeneity was achieved using macrophage colony stimulating factor supplementation (long/mL/48 h) (R&D Systems, Cat#416-ML-500), reconstituted in PBS+1% BSA (Sigma, Cat #A8806). Cells at this point are referred to as bone marrow derived macrophages (BMDMs).

In Vitro Periodontal Disease Inflammation Model

BMDMs were serum starved for 5-8 h by replacing complete media with media containing only 2% FBS. Cells were then pre-treated with 50 µM ML324 (SelleckChem, Cat #S7296), 50 µM experimental inhibitors or DMSO vehicle control for 1 hour in complete media. Pre-treated macrophages were challenged with A.aLPS for 24 hours where supernatant protein was analyzed using DuoSet IL-6 ELISA kit (R&D Systems, Cat #DY410). Purity of experimental inhibitors was confirmed to be >95% prior to in vitro evaluation via UPLC analysis.

Synthetic Chemistry

Reference is made to Scheme 1 and Table 1 above. Method A: Compounds 12, 19-24: Biphenyl benzoyl chloride (3.6 mmol) was added to aminobenzoate derivatives 17 (3 mmol) under reflux in toluene (25 mL) as previously described.[26] Reaction was refluxed for 4 h and product was evaporated under reduced pressure by adding water continually until all toluene was removed. Product was extracted from ethyl acetate rinsing with brine. The remaining organic layer was loaded onto a 25 g silica column and purified using flash chromatography with a solvent gradient from 0-100% ethyl acetate in hexanes over 25 minutes. Fractions containing product 18 were combined and identity of products were confirmed using UPLC and NMR.

The resulting ester 18 (1 mmol) was added to a microwave vial with LiOH (0.5 mmol) and dissolved in methanol and water (3:1, 10 mL). The reaction was microwave irradiated at 100° C. for 1-2 hours until the ester starting material was consumed. The reaction was acidified, evaporated under reduced pressure, and vacuum filtered rinsing with cold HCl to yield product 12, 19-24 as a white to off-white solid.

Final products were lyophilized and analyzed using UPLC for >95% purity and $^1$H NMR for identification.

Method B: Compounds 25-42 were synthesized using a modification of a previously described technique.[22] Derivatized trifluoroborates (0.25 mmol), derivatized bromobenzenes (0.25 mmol), and cesium carbonate (0.756 mmol) was combined with catalytic [1,1'-Bis(diphenylphosphino)ferrocene]dichloropalladium(II), complex with dichloromethane (0.023 mmol) and the mixture was suspended in a degassed solution of THF and water (1:10, 5 mL) in a 20 mL microwave vial. The reaction was vortexed briefly and irradiated in a biotage initiator at 100° C. for 1-2 hours until the starting material was consumed as determined by TLC as previously described. The reaction mixture was evaporated under reduced pressure, acidified using HCl and extracted 3× from DCM. The organic was dried over sodium sulfate and adsorbed onto isolute for separation using flash chromatography to yield an off white solid. The resulting ester (1 mmol) was added to a microwave vial with LiOH (0.5 mmol) and dissolved in methanol and water (3:1, 10 mL). The reaction was microwave irradiated at 100° C. for 1-2 hours until the ester starting material was consumed. The reaction was acidified, evaporated under reduced pressure, and vacuum filtered rinsing with cold HCl to yield a white solid 15.

Carboxylic acid 15 (2 mmol) was lyophilized and resuspended in dry DCE (10 mL) under nitrogen in a flame dried flask. Oxalyl chloride (3.6 mmol) and catalytic DMF (5 drops) were added to the reaction on ice and the solution was allowed to stir at room temperature for 1-24 h until gas was no longer produced. The reaction generally turned yellow upon formation of the carbonyl chloride in solution. DCE was removed under reduced pressure using rotary evaporation to yield a bright yellow residue. The residue was resuspended in dry DCM (10 mL) and in a separate flask, Aminobenzoate derivatives 17 were dissolved in dry DCM (10 mL) with TEA (8.2 equiv.). The basic aminobenzoate solution was added to the benzoyl chloride under nitrogen via cannula transfer and the reaction was stirred at room temperature under nitrogen for 1-24 h until the amine starting material was consumed as confirmed by UPLC. The reaction mixture was filtered to remove the TEA salt, and the remaining liquid was extracted from ethyl acetate, rinsing sequentially with citric acid, NaOH and brine. The remaining organic layer was loaded onto a 25 g silica column and purified using flash chromatography with a solvent gradient from 0-100% ethyl acetate in hexanes over 25 minutes. Fractions containing product 18 were combined and identity of products were confirmed using UPLC and NMR.

The resulting ester 18 (1 mmol) was added to a microwave vial with LiOH (0.5 mmol) and dissolved in methanol and water (3:1, 10 mL). The reaction was microwave irradiated at 100° C. for 1-2 hours until the ester starting material was consumed. The reaction was acidified, evaporated under reduced pressure, and vacuum filtered rinsing with cold HCl to yield product 25-42 as a white to off-white solid.

Final products were lyophilized and analyzed using UPLC for >95% purity and $^1$H NMR for identification.

Quantitative Structure Activity Relationship (QSAR) Development

The phenotypic immunosuppressive screen data was converted into binary data using statistical significance (P<0.05) determined by One-Way ANOVA compared to DMSO controls as a cutoff. Data were normalized between experiments when necessary. A contingency analysis was run on the tested compounds within MOE to identify the descriptors that were most highly correlated with activity. The top 12 descriptors from this analysis were used to map a quantitative structure activity relationship algorithm and cross-validation was conducted using a leave one out method following standard protocols. The inventors' combinatorial library was mapped to this model to predict which of the proposed compounds would be active. The model was iteratively designed as activity data became available.

The invention will be further described, without limitation, by the following numbered paragraphs:

1. A compound of Formula (I):

wherein:
$R_1$ is hydrogen, lower alkyl or alkoxy;
$R_2$ is hydrogen, lower alkyl or alkoxy;
$R_3$ is hydrogen or —COOH;
$R_4$ is hydrogen, halogen or —COOH
$R_5$ is hydrogen, halogen or —COOH;
$R_6$ is hydrogen, halogen or lower alkyl; and
$R_7$ is hydrogen, halogen or lower alkyl;
or a pharmaceutically acceptable salt thereof.
2. The compound according to paragraph 1, wherein $R_1$ is hydrogen.
3. The compound according to paragraph 1, wherein $R_1$ is methyl.
4. The compound according to paragraph 1, wherein $R_1$ is methoxy.
5. The compound according to paragraph 1, wherein $R_2$ is hydrogen.
6. The compound according to paragraph 1, wherein $R_2$ is methyl.
7. The compound according to paragraph 1, wherein $R_2$ is methoxy.
8. The compound according to paragraph 1, wherein $R_3$ is hydrogen.
9. The compound according to paragraph 1, wherein $R_3$ is —COOH.
10. The compound according to paragraph 1, wherein $R_4$ is hydrogen,
11. The compound according to paragraph 1, wherein $R_4$ is fluorine.
12. The compound according to paragraph 1, wherein $R_4$ is —COOH.
13. The compound according to paragraph 1, wherein $R_5$ is hydrogen.
14. The compound according to paragraph 1, wherein $R_5$ is fluorine.
15. The compound according to paragraph 1, wherein $R_5$ is —COOH;
16. The compound according to paragraph 1, wherein $R_6$ is hydrogen.
17. The compound according to paragraph 1, wherein $R_6$ is fluorine.
18. The compound according to paragraph 1, wherein $R_6$ is methyl.
19. The compound according to paragraph 1, wherein $R_7$ is hydrogen.
20. The compound according to paragraph 1, wherein $R_7$ is fluorine.
21. The compound according to paragraph 1, wherein $R_7$ is methyl.
22. A pharmaceutical composition, comprising a therapeutically effective amount of a compound according to paragraph 1, or a pharmaceutically acceptable salt thereof, and a pharmaceutically acceptable carrier.
23. A method for treating an inflammatory disease or disorder, comprising the step of administering a therapeutically effective amount of a compound according to paragraph 1, or a pharmaceutically acceptable salt thereof, to a patient or subject in need thereof.
24. The method according to paragraph 23, wherein the inflammatory disease or disorder is periodontal disease.
25. The method according to paragraph 23, wherein the patient or subject is a human.

REFERENCES CITED

1. Kirkpatrick, J. E.; Kirkwood, K. L.; Woster, P. M., Inhibition of the Histone Demethylase KDM4B Leads to Activation of KDM1A, Attenuates Bacterial-Induced Pro-Inflammatory Cytokine Release, and Reduces Osteoclastogenesis. *Epigenetics* 2018.
2. Silva, N.; Abusleme, L.; Bravo, D.; Dutzan, N.; Garcia-Sesnich, J.; Vernal, R.; HernÁNdez, M.; Gamonal, J., Host response mechanisms in periodontal diseases. *Journal of Applied Oral Science* 2015, 23 (3), 329-55.
3. Smiley, C. J.; Tracy, S. L.; Abt, E.; Michalowicz, B. S.; John, M. T.; Gunsolley, J.; Cobb, C. M.; Rossmann, J.; Harrel, S. K.; Forrest, J. L.; Hujoel, P. P.; Noraian, K. W.; Greenwell, H.; Frantsve-Hawley, J.; Estrich, C.; Hanson, N., Evidence-based clinical practice guideline on the nonsurgical treatment of chronic periodontitis by means of scaling and root planing with or without adjuncts. *Journal of the American Dental Association* (1939) 2015, 146 (7), 525-35.
4. Socransky, S. S.; Haffajee, A. D.; Cugini, M. A.; Smith, C.; Kent, R. L., Jr., Microbial complexes in subgingival plaque. *J Clin Periodontol* 1998, 25 (2), 134-44.
5. Mombelli, A., Microbial colonization of the periodontal pocket and its significance for periodontal therapy. *Periodontol* 2000 2018, 76 (1), 85-96.
6. Zhuang, Z.; Yoshizawa-Smith, S.; Glowacki, A.; Maltos, K.; Pacheco, C.; Shehabeldin, M.; Mulkeen, M.; Myers, N.; Chong, R.; Verdelis, K.; Garlet, G. P.; Little, S.; Sfeir, C., Induction of M2 Macrophages Prevents Bone Loss in Murine Periodontitis Models. *J Dent Res* 2018, 22034518805984.
7. Redlich, K.; Smolen, J. S., Inflammatory bone loss: pathogenesis and therapeutic intervention. *Nat Rev Drug Discov* 2012, 11 (3), 234-250.
8. Rai G, K. A., Tumber A, et al. *Discovery of ML324, a JMJD2 demethylase inhibitor with demonstrated antiviral activity*; Bethesda (Md.): National Center for Biotechnology Information (US): 2012 Dec. 17 [Updated 2013 Sep. 16].
9. Saurav Pathak, S.; Maitra, S.; Chakravarty, S.; Kumar, A., *Histone Lysine Demethylases of JMJD2 or KDM4 Family are Important Epigenetic Regulators in Reward Circuitry in the Etiopathology of Depression*. 2016; Vol. 42.
10. Sterling, T.; Irwin, J. J., ZINC 15—Ligand Discovery for Everyone. *Journal of Chemical Information and Modeling* 2015, 55 (11), 2324-2337.
11. Aldrich, C.; Bertozzi, C.; Georg, G. I.; Kiessling, L.; Lindsley, C.; Liotta, D.; Merz, K. M.; Schepartz, A.; Wang, S., The Ecstasy and Agony of Assay Interference Compounds. *Journal of Medicinal Chemistry* 2017, 60 (6), 2165-2168.
12. Lipinski, C. A., Lead- and drug-like compounds: the rule-of-five revolution. *Drug Discovery Today: Technologies* 2004, 1 (4), 337-341.

13. Charifson, P. S.; Corkery, J. J.; Murcko, M. A.; Walters, W. P., Consensus Scoring: A Method for Obtaining Improved Hit Rates from Docking Databases of Three-Dimensional Structures into Proteins. *Journal of Medicinal Chemistry* 1999, 42 (25), 5100-5109.
14. Backman, T. W. H.; Cao, Y.; Girke, T., ChemMine tools: an online service for analyzing and clustering small molecules. *Nucleic Acids Research* 2011, 39 (suppl 2), W486-W491.
15. Wang, L.; Chang, J.; Varghese, D.; Dellinger, M.; Kumar, S.; Best, A. M.; Ruiz, J.; Bruick, R.; Peña-Llopis, S.; Xu, J.; Babinski, D. J.; Frantz, D. E.; Brekken, R. A.; Quinn, A. M.; Simeonov, A.; Easmon, J.; Martinez, E. D., A small molecule modulates Jumonji histone demethylase activity and selectively inhibits cancer growth. *Nature communications* 2013, 4, 2035-2035.
16. Chu, C.-H.; Wang, L.-Y.; Hsu, K.-C.; Chen, C.-C.; Cheng, H.-H.; Wang, S.-M.; Wu, C.-M.; Chen, T.-J.; Li, L.-T.; Liu, R.; Hung, C.-L.; Yang, J.-M.; Kung, H.-J.; Wang, W.-C., KDM4B as a Target for Prostate Cancer: Structural Analysis and Selective Inhibition by a Novel Inhibitor. *Journal of Medicinal Chemistry* 2014, 57 (14), 5975-5985.
17. Backman, T. W.; Cao, Y.; Girke, T., ChemMine tools: an online service for analyzing and clustering small molecules. *Nucleic Acids Res* 2011, 39 (Web Server issue), W486-91.
18. Berry, W. L.; Janknecht, R., KDM4/JMJD2 Histone Demethylases: Epigenetic Regulators in Cancer Cells. *Cancer research* 2013, 73 (10), 2936-42.
19. Schukin, S. I.; Zinkovsky, V. G.; Zhuk, O. V., Elimination kinetics of the novel prodrug cinazepam possessing psychotropic activity in mice. *Pharmacological Reports* 2011, 63 (5), 1093-1100.
20. Peloquin, C. A.; James, G. T.; Craig, L. D.; Kim, M.; McCarthy, E. A.; Ikle, D.; Iseman, M. D., Pharmacokinetic evaluation of aconiazide, a potentially less toxic isoniazid prodrug. *Pharmacotherapy* 1994, 14 (4), 415-23.
21. Miller, W. D.; Fray, A. H.; Quatroche, J. T.; Sturgill, C. D., Suppression of a Palladium-Mediated Homocoupling in a Suzuki Cross-Coupling Reaction. Development of an Impurity Control Strategy Supporting Synthesis of LY451395. *Organic Process Research & Development* 2007, 11 (3), 359-364.
22. Chen, Z.-W.; Zhu, Y.-Z.; Ou, J.-W.; Wang, Y.-P.; Zheng, J.-Y., Metal-Free Iodine(III)-Promoted Synthesis of Isoquinolones. *The Journal of Organic Chemistry* 2014, 79 (22), 10988-10998.
23. Pettersen, E. F.; Goddard, T. D.; Huang, C. C.; Couch, G. S.; Greenblatt, D. M.; Meng, E. C.; Ferrin, T. E., UCSF Chimera—a visualization system for exploratory research and analysis. *Journal of computational chemistry* 2004, 25 (13), 1605-12.
24. Irwin, J. J.; Sterling, T.; Mysinger, M. M.; Bolstad, E. S.; Coleman, R. G., ZINC: A Free Tool to Discover Chemistry for Biology. *Journal of Chemical Information and Modeling* 2012, 52 (7), 1757-1768.
25. Zhang, X.; Goncalves, R.; Mosser, D. M., The Isolation and Characterization of Murine Macrophages. *Current protocols in immunology/edited by John E. Coligan . . . [et al.]* 2008, Chapter, Unit-14.1.
26. Hinsberger, S.; Húsecken, K.; Groh, M.; Negri, M.; Haupenthal, J.; Hartmann, R. W., Discovery of Novel Bacterial RNA Polymerase Inhibitors: Pharmacophore-Based Virtual Screening and Hit Optimization. *Journal of Medicinal Chemistry* 2013, 56 (21), 8332-8338.

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:
1. A compound of Formula (I):

wherein:
$R_1$ is hydrogen, lower alkyl or alkoxy;
$R_2$ is hydrogen, lower alkyl or alkoxy;
$R_3$ is hydrogen or —COOH;
$R_4$ is hydrogen, halogen or —COOH
$R_5$ is fluorine;
$R_6$ is hydrogen, halogen or lower alkyl; and
$R_7$ is hydrogen, halogen or lower alkyl;
with the provisos that $R_1$ and $R_2$ are not both H; $R_3$ and $R_7$ are not both H; $R_5$, $R_6$ and $R_7$ are not all F, or a pharmaceutically acceptable salt thereof.

2. The compound according to claim 1, wherein $R_1$ is hydrogen.
3. The compound according to claim 1, wherein $R_1$ is methyl.
4. The compound according to claim 1, wherein $R_1$ is methoxy.
5. The compound according to claim 1, wherein $R_2$ is hydrogen.
6. The compound according to claim 1, wherein $R_2$ is methyl.
7. The compound according to claim 1, wherein $R_2$ is methoxy.
8. The compound according to claim 1, wherein $R_3$ is hydrogen.
9. The compound according to claim 1, wherein $R_3$ is —COOH.
10. The compound according to claim 1, wherein $R_4$ is hydrogen.
11. The compound according to claim 1, wherein $R_4$ is fluorine.
12. The compound according to claim 1, wherein $R_4$ is —COOH.
13. The compound according to claim 1, wherein $R_6$ is hydrogen.
14. The compound according to claim 1, wherein $R_6$ is fluorine.
15. The compound according to claim 1, wherein $R_6$ is methyl.
16. The compound according to claim 1, wherein $R_7$ is hydrogen.
17. The compound according to claim 1, wherein $R_7$ is fluorine.
18. The compound according to claim 1, wherein $R_7$ is methyl.

19. A pharmaceutical composition, comprising a therapeutically effective amount of a compound according to claim 1, or a pharmaceutically acceptable salt thereof, and a pharmaceutically acceptable carrier.

20. A method for treating an inflammatory disease or disorder, comprising the step of administering a therapeutically effective amount of a compound according to claim 1, or a pharmaceutically acceptable salt thereof, to a patient or subject in need thereof.

21. The method according to claim 20, wherein the inflammatory disease or disorder is periodontal disease.

22. The method according to claim 20, wherein the patient or subject is a human.

\* \* \* \* \*